United States Patent [19]
Peery et al.

[11] Patent Number: 5,985,305
[45] Date of Patent: Nov. 16, 1999

[54] SUSTAINED DELIVERY OF AN ACTIVE AGENT USING AN IMPLANTABLE SYSTEM

[75] Inventors: John R. Peery, Stanford; Keith E. Dionne, Menlo Park; James B. Eckenhoff, Los Altos, all of Calif.; Felix A. Landrau, Punta Gorda, Fla.; Scott D. Lautenbach, San Mateo, Calif.; Judy A. Magruder, Mountain View, Calif.; Jeremy C. Wright, Los Altos, Calif.

[73] Assignee: Alza Corporation, Palo Alto, Calif.

[21] Appl. No.: 08/943,007

[22] Filed: Oct. 2, 1997

Related U.S. Application Data

[63] Continuation of application No. 08/791,699, Jan. 30, 1997, Pat. No. 5,728,396
[60] Provisional application No. 60/036,015, Jan. 21, 1997.

[51] Int. Cl.⁶ ............................................ A61F 13/00
[52] U.S. Cl. ........................ 424/422; 424/424; 424/473; 604/891.1
[58] Field of Search ........................ 424/473, 422, 424/424; 604/891.1

[56] References Cited

U.S. PATENT DOCUMENTS

| | | | |
|---|---|---|---|
| 3,987,790 | 10/1976 | Eckenhoff et al. | 128/260 |
| 4,865,845 | 9/1989 | Eckenhoff et al. | 424/424 |
| 5,057,318 | 10/1991 | Magruder et al. | 424/438 |
| 5,059,423 | 10/1991 | Magruder et al. | 424/438 |
| 5,112,614 | 5/1992 | Magruder et al. | 424/422 |
| 5,137,727 | 8/1992 | Eckenhoff | 424/422 |
| 5,213,809 | 5/1993 | Wright et al. | 424/473 |
| 5,234,692 | 8/1993 | Magruder et al. | 424/473 |
| 5,234,693 | 8/1993 | Magruder et al. | 424/473 |
| 5,308,348 | 5/1994 | Balaban et al. | 604/892.1 |
| 5,413,572 | 5/1995 | Wong et al. | 604/892.1 |
| 5,540,665 | 7/1996 | Mercado et al. | 604/145 |

OTHER PUBLICATIONS

Darney, Philip D., "Subdermal Progestin Implant Contraception," *Current Opinion in Obstetrics& Gyn.* (1991) 3:470–476.

BBI Newsletter, "Implantable Infusion Pumps: Technology Poised for Takeoff" (1994) vol. 17, No. 12, pp. 209–211.

Kildsig, Dane O., et al. "Theoretical Justification of Reciprocal Rate Plots in Studies of Water Vapor Transmission through Films" (1970) *J. Pharm. Sci.*, vol. 59, No. 11, pp. 1634–1637.

Morgan, P.W., "Structure and Moisture Permeability of Film–Forming Polymers," (1953) *Ind. Eng. Chem.* vol. 45, No. 10, pp. 2296–2306.

*Materials Engineering* (1972) vol. 5–72, pp. 38–45.

"Standard Specification for Epoxy Molding Compounds," *Ann. Book of ASTM Stds.* (1984) vol. 8:02, pp. 208–211.

Rogers, C.E., et al., "Permeability Valves," *Ind. & Eng. Chem.* (1957) vol. 49, No. 11, pp. 1933–1936.

*Primary Examiner*—D. Gabrielle Brouillette
*Attorney, Agent, or Firm*—Pauline Ann Clarke; Steven F. Stone; Mary Ann Dillahunty

[57] ABSTRACT

The invention is directed to a device for delivering an active agent formulation for a predetermined administration period. An impermeable reservoir is divided into a water-swellable agent chamber and an active agent formulation chamber. Fluid from the environment is imbibed through a semipermeable plug into the water-swellable agent chamber and the active agent formulation is released through a back-diffusion regulating outlet. Delivery periods of up to 2 years are achieved.

12 Claims, 6 Drawing Sheets

SUSTAINED DELIVERY OF AN ACTIVE AGENT USING AN IMPLANTABLE SYSTEM

CROSS-REFERENCE TO RELATED APPLICATIONS

This application is a continuation of application Ser. No. 08/791,699 filed Jan. 30, 1997, now U.S. Pat. No. 5,728,396, which is a continuation-in-part application of a provisional application 60/036,015 which was filed on Feb. 2, 1996 as regular U.S. application Ser. No. 08/595,761 and converted to a provisional application via a petition filed on Jan. 21, 1997.

TECHNICAL FIELD

This invention is related to the sustained delivery of a biologically active agent. More particularly, the invention is directed to an implantable delivery system for the prolonged delivery of an active agent to a fluid environment in a natural or artificial body cavity.

BACKGROUND OF THE INVENTION

Treatment of disease by prolonged delivery of an active agent at a controlled rate has been a goal in the drug delivery field. Various approaches have been taken toward delivering the active agents.

One approach involves the use of implantable diffusional systems. For example, subdermal implants for contraception are described by Philip D. Darney in *Current Opinion in Obstetrics and Gynecology* 1991, 3:470–476. Norplant® requires the placement of 6 levonorgestrel-filled silastic capsules under the skin. Protection from conception for up to 5 years is achieved. The implants operate by simple diffusion, that is, the active agent diffuses through the polymeric material at a rate that is controlled by the characteristics of the active agent formulation and the polymeric material. Darney further describes biodegradable implants, namely Capranor™ and norethindrone pellets. These systems are designed to deliver contraceptives for about one year and then dissolve. The Capranor™ systems consist of poly(ε-caprolactone) capsules that are filled with levonorgestrel and the pellets are 10% pure cholesterol with 90% norethindrone.

Implantable infusion pumps have also been described for delivering drugs by intravenous, intra-arterial, intrathecal, intraperitoneal, intraspinal and epidural pathways. The pumps are usually surgically inserted into a subcutaneous pocket of tissue in the lower abdomen. Systems for pain management, chemotherapy and insulin delivery are described in the *BBI Newsletter*, Vol. 17, No. 12, pages 209–211, December 1994. These systems provide for more accurately controlled delivery than simple diffusional systems.

One particularly promising approach involves osmotically driven devices such as those described in U.S. Pat. Nos. 3,987,790, 4,865,845, 5,057,318, 5,059,423, 5,112,614, 5,137,727, 5,234,692 and 5,234,693 which are incorporated by reference herein. These devices can be implanted into an animal to release the active agent in a controlled manner for a predetermined administration period. In general, these devices operate by imbibing fluid from the outside environment and releasing corresponding amounts of the active agent.

The above-described devices have been useful for delivering active agents to a fluid environment of use. Although these devices have found application for human and veterinary purposes, there remains a need for devices that are capable of delivering active agents, particularly potent unstable agents, reliably to a human being at a controlled rate over a prolonged period of time.

SUMMARY OF THE INVENTION

Implantable osmotic systems for delivery of an active agent to an animal are well known. Adaptation of these systems for human use raises a number of difficult issues. The size of the device may need to be decreased for human implantation. The strength of the device must be sufficient to ensure a robust system. Accurate and reproducible delivery rates and durations must be ensured and the period from implantation to start-up of delivery must be minimized. The active agent must return its purity and activity for extended periods of time at the elevated temperatures encountered in the body cavity.

Accordingly, in one aspect, the invention is a fluid-imbibing device for delivering an active agent formulation to a fluid environment of use. The device comprises a water-swellable, semipermeable material that is received in sealing relationship with the interior surface at one end of an impermeable reservoir. The device further contains an active agent to be displaced from the device when the water-swellable material swells.

In another aspect, the invention is directed to an implantable device for delivering an active agent to a fluid environment of use. The device comprises a reservoir and a back diffusion regulating outlet in a mating relationship. The flow path of the active agent comprises a pathway formed between the mating surfaces of the back diffusion regulating outlet and the reservoir.

In yet another aspect, the present invention is directed to a device for storing an active agent in a fluid environment of use during a predetermined administration period, the device comprising a reservoir containing an active agent. The reservoir is impermeable and formed at least in part from a metallic material. The portion of the reservoir contacting the active agent is non-reactive with the active agent, and is formed of a material selected from the group consisting of titanium and its alloys.

In a further aspect, the invention is an implantable fluid-imbibing active agent delivery system that comprises an impermeable reservoir. The reservoir contains a piston that divides the reservoir into an active agent containing chamber and a water-swellable agent containing chamber. The active agent containing chamber is provided with a back-diffusion regulating outlet. The water-swellable agent containing chamber is provided with a semipermeable plug. Either the plug or the outlet is releasable from the reservoir at an internal pressure that is lower than the maximum osmotic pressure generated by the water-swellable agent.

The invention is further directed to a fluid-imbibing implantable active agent delivery system where the time to start-up of delivery is less than 10% of the predetermined administration period.

In another aspect, the invention is directed to a method for preparing a fluid-imbibing implantable active agent delivery system. The method comprises injection molding a semi-permeable plug into the end of an impermeable reservoir such that the plug is protected by the reservoir.

In still another aspect, the invention is directed to an impermeable active agent delivery system for delivering an active agent that is susceptible to degradation. The reservoir contains a piston that divides the reservoir into a water-swellable agent chamber and an active agent chamber. The open end of the water-swellable agent chamber contains a semipermeable membrane and the open end of the active agent chamber contains a back-diffusion regulating outlet. The system effectively seals the active agent chamber and isolates it from the environment of use.

In a further aspect, the invention is directed to a back-diffusion regulating outlet useful in an active agent delivery system. The outlet defines a flow path wherein the length, interior cross-sectional shape and area provide for an average linear velocity of active agent that is higher than the linear inward flow of fluid in the environment of use.

The invention is also directed to a semipermeable plug useful in an active agent delivery system. The plug is water-swellable and must expand linearly in the delivery system to commence pumping upon insertion of the system into the fluid environment of use.

The invention is further directed to implantable delivery systems useful for delivering leuprolide.

BRIEF DESRIPTION OF THE DRAWINGS

The figures are not drawn to scale, but are set forth to illustrate various embodiments of the invention. Like numbers refer to like structures.

DETAILED DESCRIPTION OF THE INVENTION

The present invention provides a device for the delivery of an active agent to a fluid environment of use in which the active agent must be protected from the fluid environment until it is delivered. Prolonged and controlled delivery is achieved.

Definitions

The term "active agent" intends the active agent(s) optionally in combination with pharmaceutically acceptable carriers and, optionally additional ingredients such as antioxidants, stabilizing agents, permeation enhancers, etc.

By a "predetermined administration period" is intended a period of greater than 7 days, often between about 30 days and 2 years, preferably greater than about 1 month and usually between about 1 month and 12 months.

By the time to "start-up" of delivery is intended the time from insertion into the fluid environment of use until the active agent is actually delivered at a rate not less than approximately 70% of the intended steady-state rate.

The term "impermeable" intends that the material is sufficiently impermeable to environmental fluids as well as ingredients contained within the dispensing device such that the migration of such materials into or out of the device through the impermeable device is so low as to have substantially no adverse impact on the function of the device during the delivery period.

The term "semipermeable" intends that the material is permeable to external fluids but substantially impermeable to other ingredients contained within the dispensing device and the environment of use.

As used herein, the terms "therapeutically effective amount" or "therapeutically effective rate" refer to the amount or rate of the active agent needed to effect the desired biologic or pharmacologic effect.

The active agent delivery devices of the invention find use where the prolonged and controlled delivery of an active agent is desired. In many cases the active agent is susceptible to degradation if exposed to the environment of use prior to delivery and the delivery devices protect the agent from such exposure.

Figure 1:
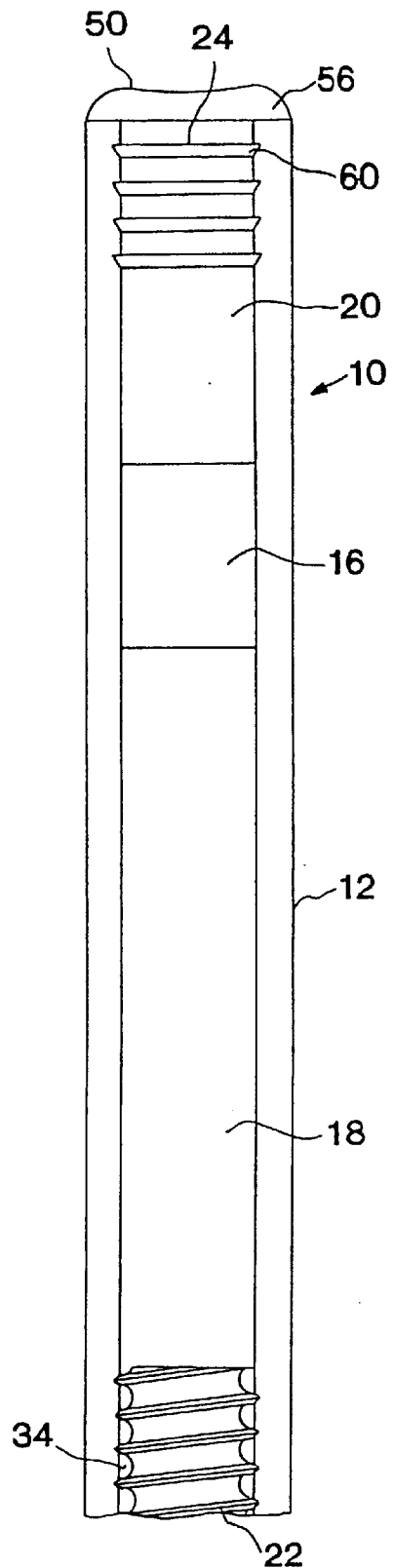
FIGS. 1 and 2 are partial cross-sectional views of two embodiments of the delivery device of the invention.
Figure 3:
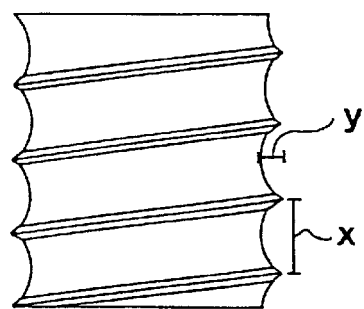
FIG. 3 is an enlarged cross-sectional view of the back-diffusion regulating outlet of FIG. 1.

FIG. 1 shows one embodiment of the device according to the invention. In FIG. 1 a fluid-imbibing system 10 is shown that comprises an impermeable reservoir 12. The reservoir 12 is divided into two chambers by a piston 16. The first chamber 18 is adapted to contain an active agent and the second chamber 20 is adapted to contain a fluid-imbibing agent. A back-diffusion regulating outlet 22 is inserted into the open end of the first compartment 18 and a water-swellable semipermeable plug 24 is inserted into the open end of the second chamber 20. In FIG. 1, the back-diffusion regulating outlet 22 is shown as a male threaded member in a mating relationship with the smooth interior surface of the reservoir 12 thereby forming therebetween helical flow path 34. The pitch (x), the amplitude (y), and the cross-sectional area and shape of the helical path 34 formed between the mating surfaces of the back-diffusion regulating outlet 22 and the reservoir 12 as shown in FIG. 3 are factors that affect both the efficiency of path 34 preventing back-diffusion of external fluid into the formulation in chamber 18 and the back pressure in the device. The geometry of outlet 22 prevents water diffusion into the reservoir. In general, it is desired that these characteristics be selected so that the length of the helical flow path 34 and the velocity of flow of active agent therethrough is sufficient to prevent back-diffusion of external fluid through the flow path 34 without significantly increasing the back pressure, so that, following start-up, the release rate of the active agent is governed by the osmotic pumping rate.

Figure 2:
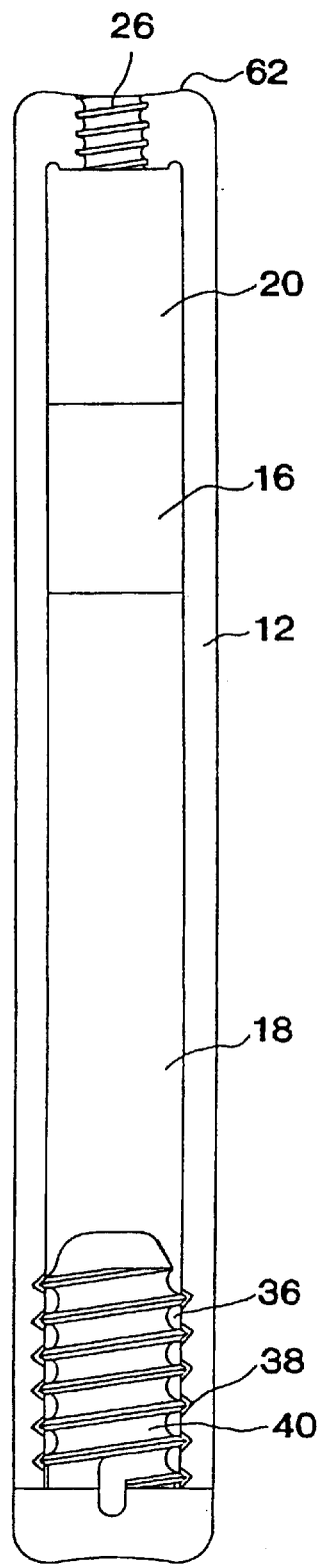

FIG. 2 is a second embodiment of the device of the invention with a reservoir 12, piston 16 and plug 26. In this embodiment, the flow path 36 is formed between a threaded back-diffusion regulating outlet 40 and threads 38 formed on the interior surface of the reservoir 12. The amplitudes of the threaded portions of the back-diffusion regulating outlet 40 and reservoir 12 are different so that a flow path 36 is formed between the reservoir 12 and the back-diffusion regulating outlet 40.

The water-swellable semipermeable plugs 24 and 26 shown in FIGS. 1 and 2 respectively are inserted into the reservoir such that the reservoir wall concentrically surrounds and protects the plug. In FIG. 1, the top portion 50 of the plug 24 is exposed to the environment of use and may form a flanged end cap portion 56 overlaying the end of reservoir 12. The semipermeable plug 24 is resiliently engaged with the interior surface of the reservoir 12 and in FIG. 1 is shown to have ridges 60 that serve to frictionally engage the semipermeable plug 24 with the interior of reservoir 12. In addition, the ridges 60 serve to produce redundant circumferential seals that function before the semipermeable plug 24 expands due to hydration. The clearance between ridges 60 and the interior surface of the reservoir 12 prevents hydration swelling from exerting stresses on the reservoir 12 that can result in tensile failure of the reservoir 12 or compression or shear failure of the plug 24. FIG. 2 shows a second embodiment of the semipermeable plug 26 where the plug is injection molded into the top portion of the reservoir and where the top of the semipermeable plug 26 is flush with the top 62 of the reservoir 12. In this embodiment, the diameter of the plug is substantially less than the diameter of the reservoir 12. In both embodiments the plugs 24 and 26 will swell upon exposure to the fluid in body cavity forming an even tighter seal with the reservoir 12.

The novel configurations of the components of the above-described embodiments provide for implantable devices that are uniquely suited for implantation into humans and can provide delivery devices which are capable of storing unstable formulations at body temperatures for extended periods of time, which devices have start-up times of less than 10% of the administration period and can be designed to be highly reliable and with predictable fail safe modes.

Reservoir 12 must be sufficiently strong to ensure that it will not leak, crack, break or distort so as to expel its active agent contents under stresses it would be subjected to during use while being impermeable. In particular, it should be designed to withstand the maximum osmotic pressure that could be generated by the water-swellable material in chamber 20. Reservoir 12 must also be chemically inert and biocompatible, that is, it must be non-reactive with the active agent formulation as well as the body. Suitable materials generally comprise a non-reactive polymer or a biocompatible metal or alloy. The polymers include acrylonitrile polymers such as acrylonitrile-butadiene-styrene terpolymer, and the like; halogenated polymers such as polytetrafluoroethylene, polychlorotrifluoroethylene, copolymer tetrafluoroethylene and hexafluoropropylene; polyimide; polysulfone; polycarbonate; polyethylene; polypropylene; polyvinylchloride-acrylic copolymer; polycarbonate-acrylonitrile-butadiene-styrene; polystyrene; and the like. The water vapor transmission rate through compositions useful for forming the reservoir are reported in *J. Pharm. Sci.*, Vol. 29, pp. 1634–37 (1970), *Ind. Eng. Chem.*, Vol. 45, pp. 2296–2306 (1953); *Materials Engineering*, Vol. 5, pp. 38–45 (1972); *Ann. Book of ASTM Stds.*, Vol. 8.02, pp. 208–211 and pp. 584–587 (1984); and *Ind. and Eng. Chem.*, Vol. 49, pp. 1933–1936 (1957). The polymers are known in the *Handbook of Common Polymers* by Scott and Roff, CRC Press, Cleveland Rubber Co., Cleveland, Ohio. Metallic materials useful in the invention include stainless steel, titanium, platinum, tantalum, gold and their alloys as well as gold-plated ferrous alloys, platinum-plated ferrous alloys, cobalt-chromium alloys and titanium nitride coated stainless steel. A reservoir made from titanium or a titanium alloy having greater than 60%, often greater than 85% titanium is particularly preferred for the most size-critical applications, for high payload capability and for long duration applications and for those applications where the formulation is sensitive to body chemistry at the implantation site or where the body is sensitive to the formulation. Preferred systems maintain at least 70% active agent after 14 months at 37° C. and have a shelf stability of at least about 9 months, or more preferably at least about two years, at 2–8° C. Most preferably, systems may be stored at room temperature. In certain embodiments, and for applications other than the fluid-imbibing devices specifically described, where unstable formulations are in chamber 18, particularly protein and/or peptide formulations, the metallic components to which the formulation is exposed must be formed of titanium or its alloys as described above.

The devices of this invention provide a sealed chamber 18 which effectively isolates the formulation from the fluid environment. The reservoir 12 is made of a rigid, impermeable and strong material. The water-swellable semipermeable plug 24 is of a lower durometer material and will conform to the shape of the reservoir to produce a liquid-tight seal with the interior of reservoir 12 upon wetting. The flow path 34 isolates chamber 18 from back-diffusion of environmental fluid. Piston 16 isolates chamber 18 from the environmental fluids that are permitted to enter chamber 20 through semipermeable plugs 24 and 26 such that, in use at steady-state flow, active agent is expelled through outlet 22 at a rate corresponding to the rate at which water from the environment flows into the water-swellable material in chamber 20 through semipermeable plugs 24 and 26. As a result, the plug and the active agent formulation will be protected from damage and their functionality will not be compromised even if the reservoir is deformed. In addition, the use of sealants and adhesives will be avoided and the attendant issues of biocompatibility and ease of manufacture resolved.

Materials from which the semipermeable plug are made are those that are semipermeable and that can conform to the shape of the reservoir upon wetting and adhere to the rigid surface of the reservoir. The semipermeable plug expands as it hydrates when placed in a fluid environment so that a seal is generated between the mating surfaces of the plug and the reservoir. The strength of the seals between the reservoir 12 and the outlet 22 and the reservoir 12 and the plugs 24 and 26 can be designed to withstand the maximum osmotic pressure generated by the device. In a preferred alternative, the plugs 24 and 26 may be designed to withstand at least 10× the osmotic agent compartment 20 operating pressure. In a further alternative the plugs 24 and 26 may be releasable from the reservoir at an internal pressure that is lower than the pressure needed to release the back diffusion regulating outlet. In this fail safe embodiment, the water-swellable agent chamber will be opened and depressurized, thus avoiding dispelling the diffusion regulating outlet and attendant release of a large quantity of the active agent. In other cases, where a fail-safe system requires the release of the active agent formulation rather than the water-swellable agent formulation, the semipermeable plug must be releasable at a pressure that is higher than the outlet.

In either case, the semipermeable plug must be long enough to sealably engage the reservoir wall under the operating conditions, that is, it should have an aspect ratio of between 1:10 and 10:1 length to diameter, preferably at least about 1:2 length to diameter, and often between 7:10 and 2:1. The plug must be able to imbibe between about 0.1% and 200% by weight of water. The diameter of the plug is such that it will sealingly fit inside the reservoir prior to hydration as a result of sealing contact at one or more circumferential zones and will expand in place upon wetting to form an even tighter seal with the reservoir. The polymeric materials from which the semipermeable plug may be made vary based on the pumping rates and device configuration requirements and include but are not limited to plasticized cellulosic materials, enhanced polymethylmethacrylate such as hydroxyethylmethacrylate (HEMA) and elastomeric materials such as polyurethanes and polyamides, polyether-polyamide copolymers, thermoplastic copolyesters and the like.

The piston 16 isolates the water-swellable agent in chamber 20 from the active agent in chamber 18 and must be capable of sealably moving under pressure within reservoir 12. The piston 16 is preferably made of a material that is of lower durometer than the reservoir 12 and that will deform to fit the lumen of the reservoir to provide a fluid-tight compression seal with the reservoir 12. The materials from which the piston are made are preferably elastomeric materials that are impermeable and include but are not limited to polypropylene, rubbers such as EPDM, silicone rubber, butyl rubber, and the like, and thermoplastic elastomers such as plasticized polyvinylchloride, polyurethanes, Santoprene®, C-Flex® TPE (Consolidated Polymer Technologies Inc.), and the like. The piston may be of a self-loading or compression-loaded design.

The back-diffusion regulating outlet 22 forms the delivery pathway through which the active agent flows from the chamber 18 to the implantation site where absorption of the active agent takes place. The seal between the outlet 22 and the reservoir 12 can be designed to withstand the maximum osmotic pressure generated within the device or to fail-safe in the modes described above. In a preferred embodiment, the pressure required to release back-diffusion regulating outlet 22 is at least 10× the pressure required to move piston 16 and/or at least 10× the pressure in chamber 18.

The exit flow path of the active agent is the pathway 34 formed between the mating surfaces of the back-diffusion regulating outlet 22 and the reservoir 12. The pathway length, interior cross-sectional shape and area of the outlet path 34 or 36 are chosen such that the average linear velocity of the exiting active agent is higher than that of the linear inward flux of materials in the environment of use due to diffusion or osmosis, thereby attenuating or moderating back-diffusion and its deleterious effects of contaminating the interior of the pump, destabilizing, diluting, or otherwise altering the formulation. The release rate of active agent can be modified by modifying the outlet pathway geometry, which relationship is shown below.

The convective flow of active agent out of outlet 22 is set by the pumping rate of the system and the concentration of active agent in chamber 20 and can be represented as follows:

$$Q_{ca} = (Q)(C_a) \tag{1}$$

where $Q_{ca}$ is the convective transport of agent A in mg/day

Q is the overall convective transport of the agent and its diluents in cm$^3$/day $C_a$ is the concentration of agent A in the formulation within chamber 20 in mg/cm$^3$ The diffusive flow of agent A through the material in the outlet 22 is a function of agent concentration, cross-sectional configuration of flow path 34 or 36, agent diffusivity and length of flow path 34 or 36, and can be represented as follows:

$$Q_{da} = D\pi r^2 \Delta C_a / L \tag{2}$$

where $Q_{da}$ is the diffusive transport of agent A in mg/day

D is the diffusivity through the material in path 34 or 36 in cm$^2$/day r is the effective inner radius of the flow path in cm $\Delta C_a$ is the difference between the concentration of agent A in the reservoir and in the body outside of the outlet 22 in mg/cm$^3$ L is the length of the flow path in cm In general, the concentration of agent in the reservoir is much greater than the concentration of agent in the body outside of the orifice such that the difference, $\Delta C_a$ can be approximated by the concentration of agent within the reservoir, $C_a$.

$$Q_{da} = D\pi r^2 C_a / L \tag{3}$$

It is generally desirable to keep the diffusive flux of agent at less than 10% of the convective flow. This is represented as follows:

$$Q_{da}/Q_{ca} = D\pi r^2 C_a / QC_a L = D\pi r^2 / QL \leq 0.1 \tag{4}$$

Figure 4:
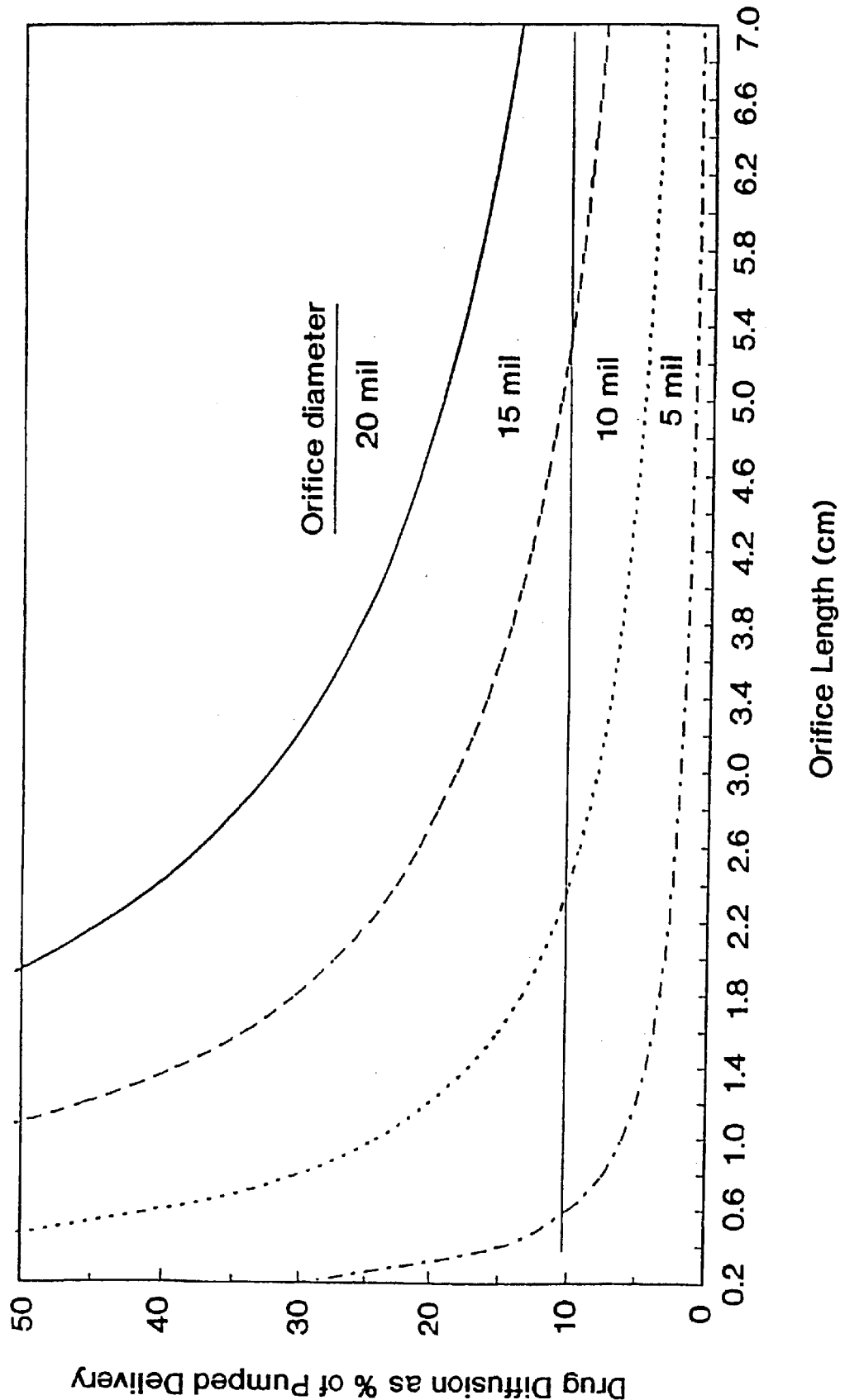
FIG. 4 is a graph that shows the effect of orifice diameter and length on drug diffusion.

Equation 4 indicates that the relative diffusive flux decreases with increasing volumetric flow rate and path length and increases with increasing diffusivity and channel radius and is independent of drug concentration. Equation 4 is plotted in FIG. 4 as a function of length (L) and diameter (d) for D=2×10$^{-6}$ $^{cm^2}$/sec and Q=0.36 μl/day.

The diffusive flux of water where the orifice opens into chamber 18 can be approximated as:

$$Q_{wd}(res) = C_o Q e^{(-QL/D_w A)} \tag{5}$$

where $C_o$ is the concentration profile of water in mg/cm$^3$

Q is the mass flow rate in mg/day

L is the length of the flow path in cm $D_w$ is the diffusivity of water through the material in the flow path in cm$^2$/day A is the cross-sectional area of the flow path in cm$^2$ The hydrodynamic pressure drop across the orifice can be calculated as follows:

$$\Delta P = \frac{8 Q L \mu}{\pi r^4} \tag{6}$$

Simultaneously solving equations (4), (5) and (6) gives the values shown in Table 1 where:

TABLE 1

Q = 0.38 μl/day
$C_a$ = 0.4 mg/μl
L = 5 cm
$D_a$ = 2.00 E-06 cm$^2$/sec
μ = 5.00 E +02 cp
$C_{wo}$ = 0 mg/μl
$D_w$ = 6.00 E + 06 cm/sec Drug Diffusion & Pulping

| Effective Orifice dia (mil) | Cross Sec area (mm$^2$) | Pump rate $QC_a$ mg/day | Diffusion $QD_a$ mg/day | Diff/Conv $OD_a/QC_a$ | Water Intrusion $OD_w$ mg/day | $OD_w$ mg/year | Pressure Drop delta P psi |
|---|---|---|---|---|---|---|---|
| 1 | 0.00051 | 0.152 | 0.0001 | 0.0005 | 0 | 0 | 1.55800 |
| 2 | 0.00203 | 0.152 | 0.0003 | 0.0018 | 1.14E−79 | 4.16E−77 | 0.09738 |
| 3 | 0.00456 | 0.152 | 0.0006 | 0.0041 | 4.79E−36 | 1.75E−33 | 0.01923 |
| 4 | 0.00811 | 0.152 | 0.0011 | 0.0074 | 8.89E−21 | 3.25E−18 | 0.00609 |
| 5 | 0.01267 | 0.152 | 0.0018 | 0.0115 | 1.04E−13 | 3.79E−11 | 0.00249 |

TABLE 1-continued $$Q = 0.38 \, \mu l/day$$
$$C_a = 0.4 \, mg/\mu l$$
$$L = 5 \, cm$$
$$D_a = 2.00 \, E{-}06 \, cm^2/sec$$
$$\mu = 5.00 \, E{+}02 \, cp$$
$$C_{wo} = 0 \, mg/\mu l$$
$$D_w = 6.00 \, E + 06 \, cm/sec$$

Drug Diffusion & Pulping

| Effective Orifice dia (mil) | Cross Sec area (mm$^2$) | Pump rate $QC_a$ mg/day | Diffusion $QD_a$ mg/day | Diff/Conv $OD_a/QC_a$ | Water Intrusion $OD_w$ mg/day | $OD_w$ mg/year | Pressure Drop delta P psi |
|---|---|---|---|---|---|---|---|
| 6  | 0.01824 | 0.152 | 0.0025 | 0.0166 | 7.16E−10 | 2.61E−07 | 0.00120 |
| 7  | 0.02483 | 0.152 | 0.0034 | 0.0226 | 1.48E−07 | 5.4E−05  | 0.00065 |
| 8  | 0.03243 | 0.152 | 0.0045 | 0.0295 | 4.7E−06  | 0.001715 | 0.00038 |
| 9  | 0.04106 | 0.152 | 0.0057 | 0.0373 | 5.04E−05 | 0.018381 | 0.00024 |
| 10 | 0.05068 | 0.152 | 0.0070 | 0.0461 | 0.000275 | 0.100263 | 0.00016 |
| 11 | 0.06132 | 0.152 | 0.0085 | 0.0558 | 0.000964 | 0.351771 | 0.00011 |
| 12 | 0.07298 | 0.152 | 0.0101 | 0.0664 | 0.002504 | 0.913839 | 0.00008 |
| 13 | 0.08584 | 0.152 | 0.0118 | 0.0779 | 0.005263 | 1.921027 | 0.00005 |
| 14 | 0.09933 | 0.152 | 0.0137 | 0.0903 | 0.00949  | 3.463836 | 0.00004 |
| 15 | 0.11402 | 0.152 | 0.0158 | 0.1037 | 0.015269 | 5.573195 | 0.00003 |
| 16 | 0.12973 | 0.152 | 0.0179 | 0.1180 | 0.022535 | 8.225224 | 0.00002 |
| 17 | 0.14646 | 0.152 | 0.0202 | 0.1332 | 0.031114 | 11.35656 | 0.00002 |
| 18 | 0.16419 | 0.152 | 0.0227 | 0.1493 | 0.040772 | 14.88166 | 0.00001 |
| 19 | 0.18295 | 0.152 | 0.0253 | 0.1664 | 0.051253 | 18.70728 | 0.00001 |
| 20 | 0.20271 | 0.152 | 0.0280 | 0.1844 | 0.062309 | 22.7427  | 0.00001 |

The calculations indicate that an orifice diameter of between about 3 and 10 mil and a length of 2 to 7 cm is optimal for a device with the operating conditions described. In a preferred embodiment, the pressure drop across the orifice is less than 10% of the pressure required to release the back-diffusion regulating outlet 22.

The back-diffusion regulating outlet 22 preferably forms a helical pathway 34 or 36 incorporating a long flow path with a means of mechanically attaching the outlet into the reservoir without using adhesives or other sealants. The back-diffusion regulating outlet is made of an inert and biocompatible material selected from but not limited to metals including but not limited to titanium, stainless steel, platinum and their alloys and cobalt-chromium alloys and the like, and polymers including but not limited to polyethylene, polypropylene, polycarbonate and polymethylmethacrylate and the like. The flow path is usually between about 0.5 and 20 cm long, preferably between about 1 and 10 cm long and between about 0.001 and 0.020 inches in diameter, preferably between about 0.003 and 0.015 inches to allow for a flow of between about 0.02 and 50 $\mu$l/day, usually 0.2 to 10 $\mu$l/day and often 0.2 to 2.0 $\mu$l/day. Additionally, a catheter or other system may be attached to the end of the back-diffusion regulating outlet to provide for delivery of the active agent formulation at a site removed from the implant. Such systems are known in the art and are described, for example, in U.S. Pat. Nos. 3,732,865 and 4,340,054 which are incorporated herein by reference. Further, the flow path design may be useful in systems other than the fluid-imbibing devices specifically described herein.

The inventive device configurations described above also allow for a minimal period of delay from start-up to steady-state flow rate. This is accomplished in part as a result of the configuration of the semipermeable plug 24 or 26. As water is imbibed by the semipermeable plug, it swells. Radial expansion is limited by the rigid reservoir 12, thus the expansion must occur linearly, thereby pushing against the water-swellable agent in chamber 18, which in turn pushes against the piston 16. This allows pumping to commence prior to the time that water reaches the water-swellable agent which otherwise would be required before pumping could commence. To facilitate reliable start-up, the flow path 34 can be precharged with the active agent in chamber 18. Further, the geometry of the outlet 22 allows for initial delivery that is influenced by the concentration gradient of drug along the length of the outlet. The start-up period is less than about 25% of the predetermined delivery period and is often less than about 10% and usually less than about 5% of the predetermined delivery period. In a preferred embodiment for a one year system, at least 70% of the steady-state flow rate is achieved by day 14.

The water-swellable agent formulation in chamber 20 is preferably a tissue tolerable formulation whose high osmotic pressure and high solubility propels the active agent over a long period of time while remaining in saturated solution in the water admitted by the semipermeable membrane. The water-swellable agent is preferably selected for tolerability by subcutaneous tissue, at least at pumping rates and hypothetically resulting concentrations to allow inadvertent dispensing from implanted devices left in the patient for a longer than labeled period. In preferred embodiments, the water-swellable agent should not diffuse or permeate through the semipermeable plug 24 or 26 to any appreciable amount (e.g., less than 8%) under normal operating conditions. Osmotic agents, such as NaCl with appropriate tabletting agents (lubricants and binders) and viscosity modifying agents, such as sodium carboxymethylcellulose or sodium polyacrylate are preferred water-swellable agents. Other osmotic agents useful as the water-swellable agent include osmopolymers and osmagents and are described, for example, in U.S. Pat. No. 5,413,572 which is incorporated by reference herein. The water-swellable agent formulation can be a slurry, a tablet, a molded or extruded material or other form known in the art. A liquid or gel additive or filler may be added to chamber 20 to exclude air from spaces around the osmotic engine. Exclusion of air from the devices should mean that delivery rates will be less affected by nominal external pressure changes (e.g., ±7 p.s.i. (±5 a.t.m.)).

The devices of the invention are useful to deliver a wide variety of active agents. These agents include but are not limited to pharmacologically active peptides and proteins, genes and gene products, other gene therapy agents, and other small molecules. The polypeptides may include but are not limited to growth hormone, somatotropin analogues, somatomedin-C, Gonadotropic releasing hormone, follicle stimulating hormone, luteinizing hormone, LHRH, LHRH analogues such as leuprolide, nafarelin and goserelin, LHRH agonists and antagonists, growth hormone releasing factor, calcitonin, colchicine, gonadotropins such as chorionic gonadotropin, oxytocin, octreotide, somatotropin plus an amino acid, vasopressin, adrenocorticotrophic hormone, epidermal growth factor, prolactin, somatostatin, somatotropin plus a protein, cosyntropin, lypressin, polypeptides such as thyrotropin releasing hormone, thyroid stimulation hormone, secretin, pancreozymin, enkephalin, glucagon, endocrine agents secreted internally and distributed by way of the bloodstream, and the like. Further agents that may be delivered include $\alpha_1$antitrypsin, factor VIII, factor IX and other coagulation factors, insulin and other peptide hormones, adrenal cortical stimulating hormone, thyroid stimulating hormone and other pituitary hormones, interferon $\alpha$, $\beta$, and $\delta$, erythropoietin, growth factors such as GCSF, GMCSF, insulin-like growth factor 1, tissue plasminogen activator, CD4, dDAVP, interleukin-1 receptor antagonist, tumor necrosis factor, pancreatic enzymes, lactase, cytokines, interleukin-1 receptor antagonist, interleukin-2, tumor necrosis factor receptor, tumor suppresser proteins, cytotoxic proteins, and recombinant antibodies and antibody fragments, and the like.

The above agents are useful for the treatment of a variety of conditions including but not limited to hemophilia and other blood disorders, growth disorders, diabetes, leukemia, hepatitis, renal failure, HIV infection, hereditary diseases such as cerbrosidase deficiency and adenosine deaminase deficiency, hypertension, septic shock, autoimmune diseases such as multiple sclerosis, Graves disease, systemic lupus erythematosus and rheumatoid arthritis, shock and wasting disorders, cystic fibrosis, lactose intolerance, Crohn's diseases, inflammatory bowel disease, gastrointestinal and other cancers.

The active agents may be anhydrous or aqueous solutions, suspensions or complexes with pharmaceutically acceptable vehicles or carriers such that a flowable formulation is produced that may be stored for long periods on the shelf or under refrigeration, as well as stored in an implanted delivery system. The formulations may include pharmaceutically acceptable carriers and additional inert ingredients. The active agents may be in various forms, such as uncharged molecules, components of molecular complexes or pharmacologically acceptable salts. Also, simple derivatives of the agents (such as prodrugs, ethers, esters, amides, etc.) which are easily hydrolyzed by body pH, enzymes, etc., can be employed.

It is to be understood that more than one active agent may be incorporated into the active agent formulation in a device of this invention and that the use of the term "agent" in no way excludes the use of two or more such agents. The dispensing devices of the invention find use, for example, in humans or other animals. The environment of use is a fluid environment and can comprise any subcutaneous position or body cavity, such as the peritoneum or uterus, and may or may not be equivalent to the point of ultimate delivery of the active agent formulation. A single dispensing device or several dispensing devices can be administered to a subject during a therapeutic program. The devices are designed to remain implanted during a predetermined administration period. If the devices are not removed following the administration, they may be designed to withstand the maximum osmotic pressure of the water-swellable agent or they may be designed with a bypass to release the pressure generated within the device.

The devices of the present invention are preferably rendered sterile prior to use, especially when such use is implantation. This may be accomplished by separately sterilizing each component, e.g., by gamma radiation, steam sterilization or sterile filtration, then aseptically assembling the final system. Alternatively, the devices may be assembled, then terminally sterilized using any appropriate method.

PREPARATION OF THE DEVICES OF THE INVENTION

Figure 7:
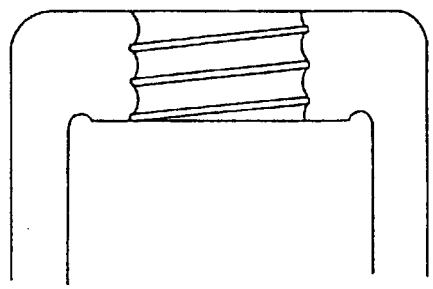
FIGS. 5, 6, 7 and 8 are enlarged cross-sectional views of further embodiments of the semipermeable plug end of the reservoir according to the invention.
Figure 8:
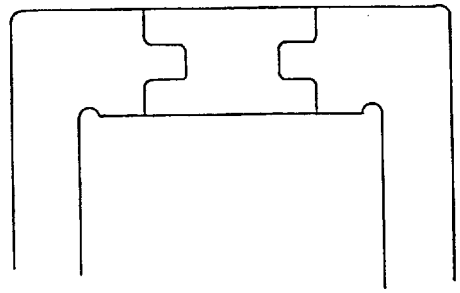
Figure 5:
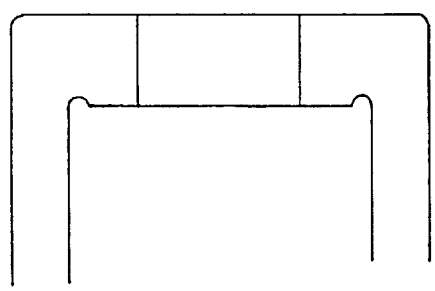
Figure 6:
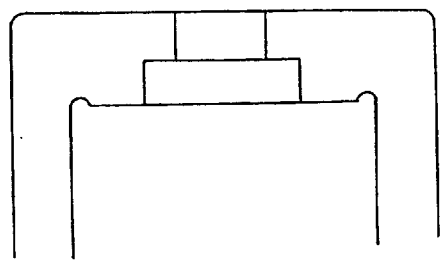

Reservoir 12 is prepared preferably by machining a metal rod or by extrusion or injection molding a polymer. The top portion of the reservoir may be open as shown in FIG. 1 or may contain a cavity as shown in FIG. 2.

Where the reservoir 12 is open as shown in FIG. 1, a water-swellable semipermeable plug 24 is inserted mechanically from the outside of the reservoir without using an adhesive before or after insertion of the piston and water-swellable agent formulation. Reservoir 12 may be provided with grooves or threads which engage ribs or threads on plug 24.

Where the reservoir 12 contains a cavity as shown in FIG. 2, the cavity may be cylindrical in shape, as shown in FIG. 5, it may be stepped, as shown in FIG. 6, it may be helical, as shown in FIG. 7 or it may be in a spaced configuration, as shown in FIG. 8. The semipermeable plug 26 is then injected, inserted, or otherwise assembled into the cavity so that it forms a seal with the reservoir wall.

Following insertion of the plug 26 either mechanically, by welding or by injection, the water-swellable agent is assembled into the reservoir followed by insertion of the piston, with appropriate steps taken to vent entrapped air. The active agent is filled into the device using a syringe or a precision dispensing pump. The diffusion moderator is inserted into the device, usually by a rotating or helical action, or by axial pressing.

The following examples are illustrative of the present invention. They are not to be construed as limiting the scope of the invention. Variations and equivalents of these examples will be apparent to those of skill in the art in light of the present disclosure, the drawings and claims herein.

EXAMPLES

Example 1

Preparation of a Device with an HDPE Reservoir

A system containing leuprolide acetate for the treatment of prostate cancer was assembled from the following components:

Reservoir (HDPE) (5 mm outside diameter, 3 mm inside diameter)

Piston (Santoprene®)

Lubricant (silicone medical fluid)

Compressed osmotic engine (60% NaCl, 40% sodium carboxymethyl cellulose)

Membrane plug (Hytrel polyether-ester block copolymer, injection molded to desired shape)

Back diffusion Regulating Outlet (polycarbonate)

Active agent (0.78 g of 60% propylene glycol and 40% leuprolide acetate)

Assembly

The piston and inner diameter of the reservoir were lightly lubricated with silicon medical fluid. The piston 16 was inserted into the open end of chamber 20. Two osmotic engine tablets (40 mg each) were then inserted on top of piston 16. After insertion, the osmotic engine was flush with the end of the reservoir. The membrane plug 24 was inserted by lining up the plug with the reservoir and pushing gently until the plug was fully engaged in the reservoir. Active agent was loaded into a syringe which was then used to fill chamber 18 from its open end by injecting the material into the open tube until the formulation was ~3 mm from the end. The filled reservoir was centrifuged (outlet end "up") to remove any air bubbles that have been trapped in the formulation during filling. The outlet 22 was screwed into the open end of the reservoir until completely engaged. As the outlet was screwed in, excess formulation exited out of the orifice ensuring a uniform fill.

Example 2

Insertion of the Device of Example 1

Insertion of the device of Example 1 is done under aseptic conditions using a trocar similar to that used in the implantation of Norplant® contraceptive implants to position the device under the skin. The insertion area is typically in the inside of the upper arm, 8 to 10 cm above the elbow.

The area is anesthetized and an incision is made through the skin. The incision is approximately 4 mm long. The trocar is inserted into the incision until the tip of the trocar is at a distance of 4 to 6 cm from the incision. The obturator is then removed from the trocar and the device of Example 1 inserted into the trocar. The device is then advanced to the open end of the trocar using the obturator. The obturator is then held in position, thus immobilizing the device of Example 1 while the trocar is withdrawn over both the device and the obturator. The obturator is then removed, leaving the implant behind in a well-controlled position. The edges of the incision are then secured with a skin closure. The area is covered and kept dry for 2 to 3 days.

Example 3

Removal of the Device of Example 1

The device of Example 1 is removed as follows: The device is located by fingertip palpation of the upper arm area. The area at one end of the implant is then anesthetized and an approximately 4 mm, perpendicular incision is made through the skin and any fibrous capsule tissue surrounding the implant area. The end of the device opposite the incision is pushed so that the device end proximal to the incision is urged out of the incision. Any further fibrotic tissue is cut with a scalpel. Following removal, the procedure of Example 2 can be followed to insert a new device.

Example 4

Delivery Rate of the Device of Example 1

Figure 9:
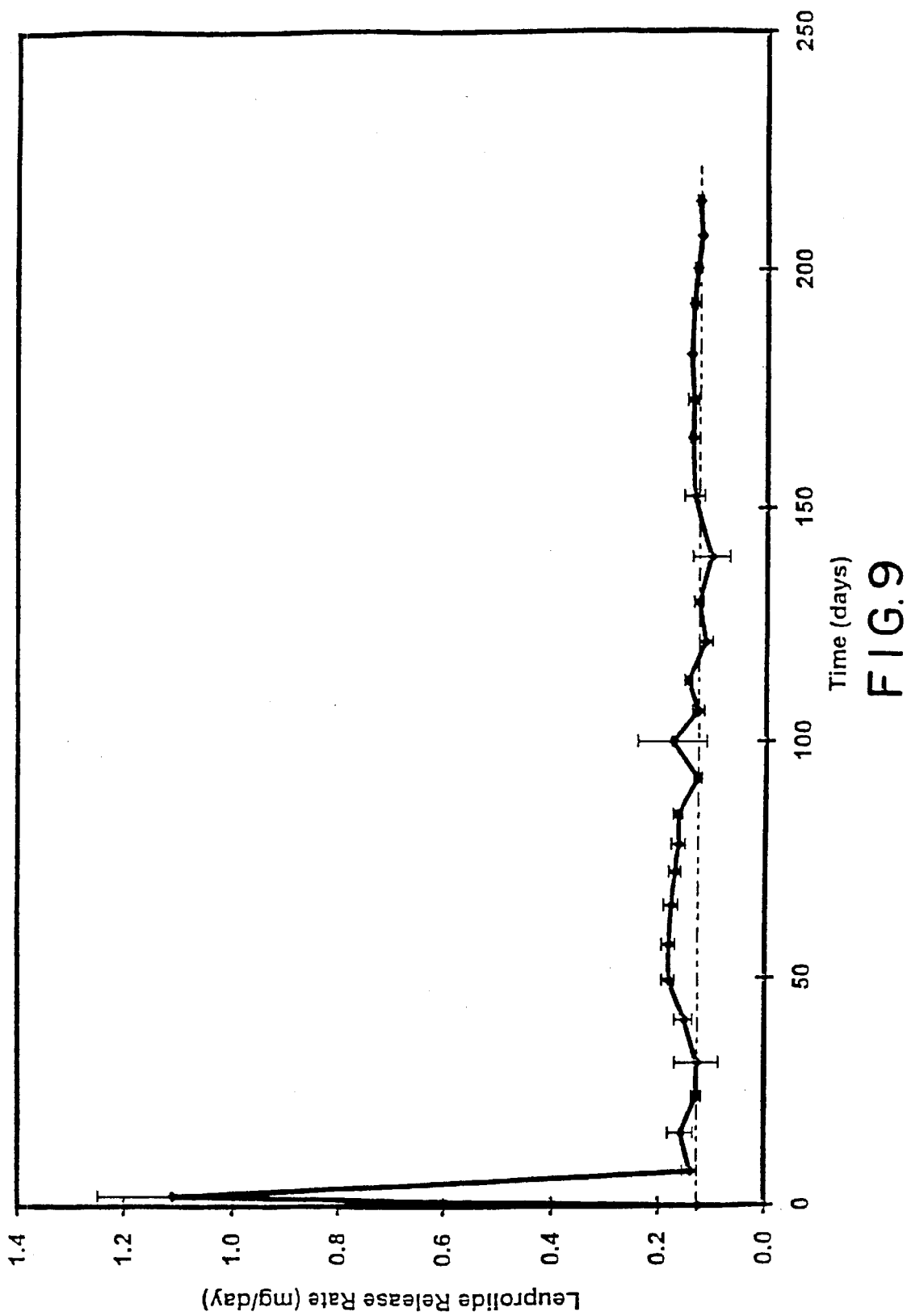
FIGS. 9, 10 and 11 are graphs of release rates for systems with leuprolide (FIG. 9) and with blue dye and with different membranes (FIGS. 10 and 11).

Glass test tubes were filled with 35 ml distilled water and then placed in a 37° C. water bath. A single device as described in Example 1 was placed in each test tube and the test tubes were changed periodically. The delivery rate profile from the system is shown in FIG. 9. The system does not have any start-up time because the system exhibits a period of initial high release followed by a lower steady state release for a period of 200 days.

Example 5

Delivery Rate Profiles

Figure 10:
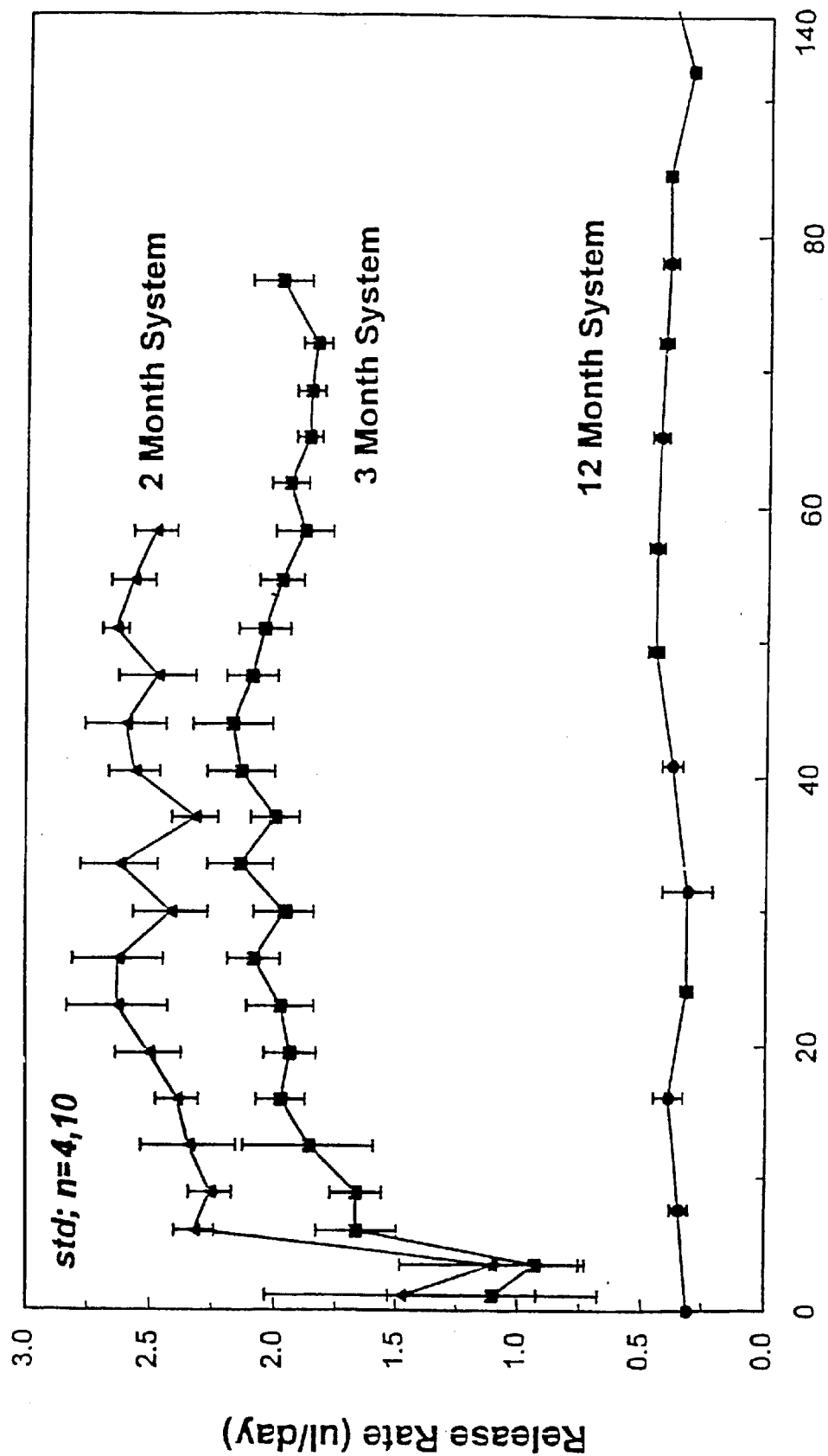
Figure 11:
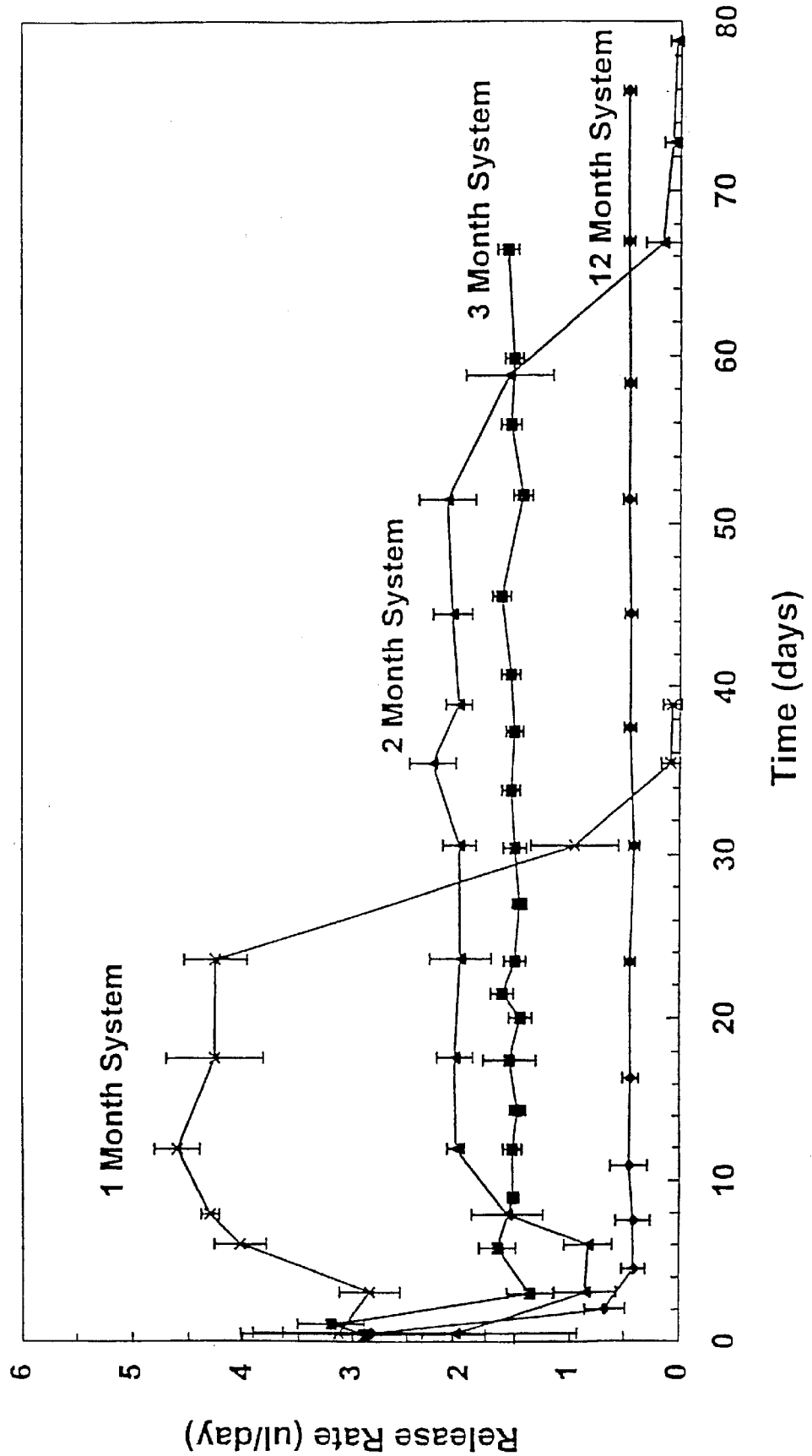

Glass test tubes were filled with 35 ml distilled water which were then placed in a 37° C. water bath. After the test tubes had come up to temperature, a single device as described in Example 1, but with membrane materials described below and containing 1% FD&C blue dye in water as the drug formulation, was placed in each tube. Water from the test tube permeated through the membrane causing the system to pump formulation (blue dye) into the surrounding water in the test tube. At regular intervals, systems were switched to fresh test tubes. The amount of dye released was determined by measuring the concentration of blue dye in each test tube using a spectrophotometer. The pumping rate was calculated from the total dye released, the volume of water in the tube, the initial concentration of dye and the interval over which the system was in the test tube. Results for two different tests are shown in FIGS. 10 and 11. FIG. 10 shows 3 different systems with different plug materials (Hytrel® 2, 3 and 12 month systems) and FIG. 11 shows 4 systems with different plug materials. These materials are:

| Membrane | Material |
| --- | --- |
| 1 month | Pebax 25 (Polyamide) |
| 2 month | Pebax 22 (Polyamide) |
| 3 month | Polyurethane (HP60D) |
| 12 month | Pebax 24 (Polyamide) |

The systems were capable of delivering for a period of from 2 to 12 months, depending on the membrane used.

Example 6

Preparation of a Delivery Device with a Titanium Reservoir

A system containing leuprolide acetate for the treatment of prostate cancer was assembled from the following components:

Reservoir (Titanium, Ti6Al4V alloy) (4 mm outside diameter, 3 mm inside diameter)

Piston (C-Flex®)

Lubricant (silicone medical fluid)

Compressed osmotic engine (76.4% NaCl, 15.5% sodium carboxymethyl cellulose, 6% povidone, 0.5% Mg Stearate, 1.6% water)

PEG 400 (8 mg added to osmotic engine to fill air spaces)

Membrane plug (polyurethane polymer, injection molded to desired shape)

Back diffusion Regulating Outlet (polyethylene)

Drug formulation (0.150 g of 60% water and 40% leuprolide acetate)

Assembly

The piston and inner diameter of the reservoir were lightly lubricated. The piston was inserted ~0.5 cm into the reservoir at the membrane end. PEG 400 was added into the reservoir. Two osmotic engine tablets (40 mg each) were then inserted into the reservoir from the membrane end. After insertion, the osmotic engine was flush with the end of the reservoir. The membrane plug was inserted by lining up the plug with the reservoir and pushing gently until the retaining features of the plug were fully engaged in the reservoir. Formulation was loaded into a syringe which was then used to fill the reservoir from the outlet end by injecting formulation into the open tube until the formulation was ~3 mm from the end. The filled reservoir was centrifuged (outlet end "up") to remove any air bubbles that have been trapped in the formulation during filling. The outlet was screwed into the open end of the reservoir until completely engaged. As the outlet was screwed in, excess formulation exited out of the orifice ensuring a uniform fill.

Example 7

Preparation of a Leuprolide Acetate Delivery Device with a Titanium Reservoir

A system containing leuprolide acetate for the treatment of prostate cancer was assembled from the following components:

Reservoir (Titanium Ti6Al4V alloy) (4 mm outside diameter, 3 mm inside diameter, 4.5 cm length)

Piston (C-Flex® TPE elastomer, available from Consolidated Polymer Technologies, Inc.)

Lubricant (silicone medical fluid 360)

Compressed osmotic engine tablet (76.4% NaCl, 15.5% sodium carboxymethyl cellulose, 6% povidone, 0.5% Mg Stearate, 1.5% water, 50 mg total)

PEG 400 (8 mg added to osmotic engine to fill air spaces)

Membrane plug (polyurethane polymer 20% water uptake, injection molded to desired shape 3 mm diameter×4 mm length)

Back-diffusion Regulating Outlet (polyethylene, with 6 mil×5 cm channel)

Drug formulation (leuprolide acetate dissolved in DMSO to a measured content of 65 mg leuprolide)

Assembly

Systems were assembled as in Example 6, using aseptic procedures to assemble γ-irradiated subassemblies and filled aseptically with sterile filtered leuprolide DMSO formulation.

Release Rate

These systems delivered about 0.35 $\mu$L/day leuprolide formulation containing on average 150 $\mu$g leuprolide in the amount delivered per day. They provide delivery of leuprolide at this rate for at least one year. The systems achieved approximately 70% steady-state delivery by day 14.

Implantation and Removal

Systems will be implanted under local anesthetic and by means of an incision and trocar as in Example 2 to patient suffering from advanced prostatic cancer.

After one year, systems will be removed under local anesthetic as described in Example 3. New systems may be inserted at that time.

Example 8

Treatment of Prostatic Cancer

Leuprolide acetate, an LHRH agonist, acts as a potent inhibitor of gonadotropin secretion when given continuously and in therapeutic doses. Animal and human studies indicate that following an initial stimulation, chronic administration of leuprolide acetate results in suppression of testicular steroidogenesis. This effect is reversible upon discontinuation of drug therapy. Administration of leuprolide acetate has resulted in inhibition of the growth of certain hormone-dependent tumors (prostatic tumors in Noble and Dunning male rats and DMBA-induced mammary tumors in female rats) as well as atrophy of the reproductive organs. In humans, administration of leuprolide acetate results in an initial increase in circulating levels of luteinizing hormone (LH) and follicle stimulating hormone (FSH), leading to a transient increase in levels of the gonadal steroids (testosterone and dihydrotestosterone in males). However, continuous administration of leuprolide acetate results in decreased level of LH and FSH. In males, testosterone is reduced to castrate levels. These decreases occur within two to six weeks after initiation of treatment, and castrate levels of testosterone in prostatic cancer patients have been demonstrated for multiyear periods. Leuprolide acetate is not active when given orally.

Systems will be prepared as in Example 7, then inserted as described. The continuous administration of leuprolide for one year using these systems will reduce testosterone to castrate levels.

The above description has been given for ease of understanding only. No unnecessary limitations should be understood therefrom, as modifications will be obvious to those skilled in the art.

We claim:

1. An implantable device for delivering an active agent to a fluid environment of use, said device comprising a reservoir and a back-diffusion regulating outlet in mating relationship, wherein a flow path for the active agent comprises a pathway formed between the mating surfaces of the reservoir and the back-diffusion regulating outlet.

2. The device of claim 1 where the active agent is delivered at a rate of 0.02 to 50 $\mu$l/day.

3. The device of claim 1 wherein the active agent is selected from the group consisting of a protein, a peptide or a gene therapy agent.

4. The device of claim 3 wherein the active agent is leuprolide.

5. The device of claim 1 wherein the active agent is delivered to a site remote from the device.

6. An implantable fluid-imbibing active agent delivery system comprising an impermeable reservoir and containing a piston that divides the reservoir into an active agent containing chamber and a water-swellable agent containing chamber, wherein the active agent containing chamber is provided with a back-diffusion regulating outlet and the water-swellable agent containing chamber is provided with a semipermeable plug; wherein the plug is releasable from the reservoir at an internal pressure that is lower than the maximum osmotic pressure generated by the water-swellable agent.

7. An implantable fluid-imbibing active agent delivery system comprising an impermeable reservoir and containing a piston that divides the reservoir into an active agent containing chamber and a water-swellable agent containing chamber, wherein the active agent containing chamber is provided with a back-diffusion regulating outlet and the water-swellable agent containing chamber is provided with a semipermeable plug; wherein the outlet is releasable from the reservoir at an internal pressure that is lower than the maximum osmotic pressure generated by the water-swellable agent.

8. An implantable active agent delivery system for delivering an active agent to a fluid environment of use, said agent being susceptible to degradation if exposed to the fluid environment of use prior to delivery, said system comprising:

(a) a piston that divides the system into a first and second chamber, the first and second chambers each having an open end;

(b) a water-swellable agent formulation in the first chamber;

(c) an active agent formulation in the second chamber;

(d) a semipermeable plug in the open end of the first chamber; and (e) a back-diffusion regulating outlet in the open end of the second chamber;

wherein said system effectively seals the active agent chamber and isolates it from the environment of use.

9. The system of claim 8 wherein the active agent is selected from the group consisting of a protein, a peptide or a gene therapy agent.

10. The system of claim 8 wherein the active agent is leuprolide.

11. A back-diffusion regulating outlet useful in an active agent delivery system for delivering active agent to a fluid environment of use, said outlet defining a flow path wherein the length, interior cross-sectional shape and area provide for an average linear velocity of the active agent that is higher than the linear inward flux of the fluid environment of use.

12. The outlet of claim 11 wherein the flow path is helical in shape.

* * * * *